United States Patent
Chung et al.

(10) Patent No.: US 6,893,641 B2
(45) Date of Patent: May 17, 2005

(54) GANODERMA LUCIDUM SPORES FOR TREATMENT OF AUTOIMMUNE DISEASES

(76) Inventors: Chee-Keung Chung, Room 2018, Argyle Centre, 688 Nathan Rd., Mongkok, Kowloon (HK); Siu Kan Tong, 2018, Argyle Centre, 688 Nathan Rd., Mongkok, Kowloon (HK)

(*) Notice: Subject to any disclaimer, the term of this patent is extended or adjusted under 35 U.S.C. 154(b) by 70 days.

(21) Appl. No.: 10/234,103

(22) Filed: Sep. 5, 2002

(65) Prior Publication Data

US 2003/0143246 A1 Jul. 31, 2003

Related U.S. Application Data

(60) Continuation-in-part of application No. 09/802,862, filed on Mar. 12, 2001, now Pat. No. 6,468,542, which is a division of application No. 09/524,508, filed on Mar. 13, 2000, now Pat. No. 6,316,002.
(60) Provisional application No. 60/158,377, filed on Oct. 12, 1999.

(51) Int. Cl.[7] .............................................. A61K 35/84
(52) U.S. Cl. .................................. 424/195.15; 514/885
(58) Field of Search ...................... 424/195.15; 514/885

(56) References Cited

U.S. PATENT DOCUMENTS 5,334,704 A * 8/1994 Tsunoo et al. .............. 530/371
6,316,002 B1   11/2001 Liu et al.
6,468,542 B2 * 10/2002 Liu et al. ............... 424/195.15

FOREIGN PATENT DOCUMENTS

JP      63109754 A   *  5/1988
WO     WO 02/11744 A1   2/2002

OTHER PUBLICATIONS

Zhang et al. Zhongguo Mianyixue ZaZhi. 1994. vol. 10, No. 3, pp. 169–172, CAPLUS abstract enclosed.*
Ling–Hua et al. Phytotherapy Research. 1993. vol. 7, No. 2, pp. 203–204.*
Satoh, M. et al.; Induction of Lupus–associated Autoantibodies in BALB/c Mice by Intraperitoneal Injection of Pristane; J. Exp. Med., vol. 180, pp. 2341–2346, Dec. 1994.
Patocka, J.; Anti–Inflammatory Triterpenoids from Mysterious Mushroom Ganoderma Lucidum and Their Potential Possibility in Modern Medicine; Acta Medica, vol. 42, pp. 123–125, (1999).
Yu, S. et al.; "An experimental study on the effects of lingzhi spore on the immune function and 60Co radioresistance in micel!", China Journal of Chinese Materia Medica, Oct. 1997, vol. 22, No. 10, pp. 625–626.
Lei, N–S et al.; "Prevention of autoantibody formation and prolonged survival in New Zealand Black/New Zealand White F1 mice with an ancient Chinese herb, Ganodema tsugae"; Lupus, 2001, vol. 10, No. 7, pp. 461–465.
Moroni, G.; "Combination treatment in autoimmune diseases: systemic lupus erythematosus"; Springer Seminars in Immunopathology, 2001, vol. 23, No. 1–2, pp. 75–89.

* cited by examiner

*Primary Examiner*—Christopher R. Tate
(74) *Attorney, Agent, or Firm*—Fei-Fei Chao; BIngham McCutchen LLP

(57) ABSTRACT

The present invention provides a method for treating a mammal with immunological disorders, particularly autoimmune disease, and most preferably systemic lupus erythematosus (SLE). The method includes oral administration of germination activated *Ganoderma lucidum* spores ("GLSs") to the mammal. Additionally, a corticosteroid, such as prednisolone, can be co-administered with the GLSs to the mammal to achieve synergistic effect of treatment.

20 Claims, No Drawings

GANODERMA LUCIDUM SPORES FOR TREATMENT OF AUTOIMMUNE DISEASES

CROSS-REFERENCE TO RELATED APPLICATIONS

The present application is a continuation-in-part (CIP) of U.S. patent application Ser. No. 09/802,862, filed on Mar. 12, 2001 now U.S. Pat. No. 6,468,542, which is a divisional application of U.S. patent application Ser. No. 09/524,508, filed on Mar. 13, 2000 and issued as U.S. Pat. No. 6,316,002, which in turn claims the priority of U.S. provisional application No. 60/158,377, filed on Oct. 12, 1999, wherein all of the U.S. priority applications are herein incorporated by reference.

FIELD OF THE INVENTION

The present invention relates to a method for treating mammals with immunological disorders, particularly autoimmune diseases, and most favorably systemic lupus erythematosus (SLE), by orally administering germination activated *Ganoderma lucidum* spores ("GLSs") to the mammals. The GLSs can be co-administered with a corticosteroid to achieve a better therapeutic effect on treatment of SLE.

BACKGROUND OF THE INVENTION

The ability of the immune system to discriminate between "self" and "non-self" antigens is vital to the functioning of the immune system as a specific defense against invading microorganisms. "Non-self" antigens are those antigens on substances entering or in the body which are detectably different or foreign from the animal's own constituents, whereas "self" antigens are those which, in the healthy animal, are not detectably different or foreign from its own constituents. However, under certain conditions, including in certain disease states, an individual's immune system may identify its own constituents as "non-self," and initiate an immune response against "self" material. This, at times, may result in causing more damage or discomfort as from an invading microbe or foreign material, and often producing serious illness in an individual.

Autoimmune disease results when an individual's immune system attacks his own organs or tissues, producing a clinical condition associated with the destruction of that tissue, as exemplified by diseases such as rheumatoid arthritis, insulin-dependent diabetes mellitus, acquired immunodeficiency syndrome ("AIDS"), hemolytic anemias, rheumatic fever, Crohn's disease, Guillain-Barre syndrome, psoriasis, thyroiditis, Graves' disease, myasthenia gravis, glomerulonephritis, autoimmune hepatitis, multiple sclerosis, systemic lupus erythematosus, etc. Blocking, neutralizing or inhibiting the immune response or removing its cause in these cases is, therefore, desirable.

Autoimmune disease may be the result of a genetic predisposition alone or as the result of the influence of certain exogenous agents such as, viruses, bacteria, or chemical agents, or as the result of the action of both. Some forms of autoimmunity come about as the result of trauma to an area usually not exposed to lymphocytes, such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of the individual to antigens which are antigenically similar to, that is cross-reactive with, the individual's own tissue. For example, in rheumatic fever an antigen of the streptococcal bacterium, which causes rheumatic fever, is cross-reactive with parts of the human heart. The antibodies cannot differentiate between the bacterial antigens and the heart muscle antigens, consequently cells with either of those antigens can be destroyed.

Other autoimmune diseases, for example, insulin-dependent diabetes mellitus (involving the destruction of the insulin producing beta-cells of the islets of Langerhans), multiple sclerosis (involving the destruction of the conducting fibers of the nervous system) and rheumatoid arthritis (involving the destruction of the joint lining tissue), are characterized as being the result of a mostly cell-mediated autoimmune response and appear to be due primarily to the action of T-cells. Yet others, such as myesthenia gravis and systemic lupus erythematosus, are characterized as being the result of primarily a humoral autoimmune response.

Nevertheless, the autoimmune diseases share a common underlying pathogenesis, resulting in the need for safe and effective therapy. Yet none of the presently available drugs are completely effective for the treatment of autoimmune disease, and most are limited by severe toxicity.

Systemic lupus erythematosus (SLE), commonly known as Lupus, is an autoimmune disease characterized by dysregulation of the immune system resulting in the production of antinuclear antibodies, the generation of circulating immune complexes, and the activation of the complement system. The immune complexes build up in the tissues and joints causing inflammation, and degradation to both joints and tissues. While the word "systemic" correctly suggests that the disease effects the entire body and most organ systems, the disease most often involves inflammation and consequent injury to the joints, skin, kidney, brain, the membranes in body cavities, lung, heart, and gastrointestinal tract. An individual with SLE often experiences unpredictable acute episodes or "outbreaks" and equally unexpected remissions. The pathologic hallmark of the disease is recurrent, widespread, and diverse vascular lesions resembling a rash or changes on the surface of the skin.

Physicians have known Lupus since 1828 when it was first described by the French dermatologist, Biett. Early studies were simply descriptions of the disease, with emphasis on the skin rashes typically present in those afflicted with the disease as well as other easily visible symptoms. Forty-five years later a dermatologist named Kaposi noted that some patients with lupus erythematosus (LE) skin lesions showed signs of affected internal organs. In the 1890s, Sir William Osler, a Canadian physician, observed that SLE could affect internal organs without the occurrence of skin changes. In 1948, Dr. Malcolm Hargraves of the Mayo Clinic isolated and described the particular morphology of the LE cell. This cell was found in the blood of patients with SLE. Dr. Hargraves' discovery has enabled physicians to identify many more cases of SLE by using a simple blood test. As a result, the number of SLE cases diagnosed has steadily risen.

SLE is not a rare disorder. Although reported in both the extremely old and the extremely young, the disease is chiefly found in women of childbearing age. Among children the occurrence of SLE is three times more likely in females than in males. In the 60% of SLE patients who experience the onset of this disease between puberty and the fourth decade of life, the female to male ratio is 9:1. Thereafter, the female preponderance again falls to that observed in prepubescent children (i.e., 3:1). In addition, the disorder appears to be three times more common in persons of African and Asian descent than in persons of Caucasian descent.

The prevalence of SLE in the United States is an issue of some debate. Estimates of occurrence range from 250,000 to 2,000,000 persons. Problems with identifying SLE are part of the problem in providing estimates of the numbers of individuals affected. The root of this identification problem is the fact that the clinical features of SLE can be mimicked by many other disorders, such as infectious mononucleosis or lymphoma. In this way the actual number of individuals affected is masked.

Numerous autoantibodies (i.e., self-reactive antibodies) of differing specificity are present in SLE. SLE patients often produce autoantibodies having anti-DNA, anti-RNP, anti-Ro (SSA), and anti-Sm, anti-La (SSB) specificity and which are capable of initiating clinical features of the disease, such as glomerulonephritis, arthritis, serositis, complete heart block in newborns, and hematologic abnormalities. These autoantibodies are also possibly related to central nervous system disturbances. Kidney damage, measured by the amount of proteinuria in the urine, is one of the most acute areas of damage associated with pathogenicity in SLE, and accounts for at least 50% of the mortality and morbidity of the disease. The presence of antibodies immunoreactive with double-stranded native DNA is normally used as a diagnostic marker for SLE.

Currently, there are no really curative treatments for patients that have been diagosed with SLE. Physicians generally employ a number of powerful immunosuppressive drugs such as high-dose corticosteroids, azathioprine or cyclophosphamide—many of which have potentially harmful side effects to the patients being treated. In addition, these immunosuppressive drugs interfere with the person's ability to produce all antibodies, not just the self-reactive anti-DNA antibodies. Immunosuppressants also weaken the body's defense against other potential pathogens thereby making the patient extremely susceptible to infection and other potentially fatal diseases, such as cancer. In some of these instances, the side effects of current treatment modalities can be fatal.

Ganoderma (Ganoderma lucidum Leyss ex Fr. Karst) is a polyporous fungus. It belongs to the class Basidiomycetes, the family Polypolaceae, and the genus Ganoderma. Since ancient times, ganoderma has been praised as a miracle fungus for its capability of prolonging human life. It is believed that the medicinal effects of ganoderma lie upon the natural or bioactive substances it produces which can stimulate or modulate the neuro-endocrino-immuno system of human body to fight off diseases. Ganoderma is also well known for its antitumor and immune enhancing properties, (Kim et al., Int. J. Mol. Med. (1999), 4(3):273–277), cardiovascular effects (Lee et al., Chem. Pharm. Bull. (1990), 38:1359–1364), as well as free radical scavenging and antihepatotoxic activities (Lin et al., J. Ethnopharmacol., (1995), 47(1):33–41).

Ganoderma is the most rare and valuable herb in Chinese medicine. It is known in China for over 5,000 years as "ling zhi". There are a variety of ganoderma, for instance, G. lucidum (red), G. applanatum (brown), G. tsugae (red), G. sinense (black), and G. oregonense (dark brown). However, due to the fact that wild types of ganoderma only grow naturally and very rarely on aged trees in steep mountains, research which requires a constant supply of high quantity and quality of ganoderma has rarely been conducted.

Although it is believed that the spores of ganoderma represent the essence of ganoderma because they contain all the bioactive substances of ganoderma, most of the ganoderma studies are conducted using the fruit body or mycelium of ganoderma as experimental materials. Ganoderma spores are rarely studied.

Ganoderma spores are tiny and mist-like spores of 5~8 μm in sizes which have extremely hard and resilient, double-layer epispores, thus making them difficult to break open. The ganoderma spores normally scatter at the pelius of mature ganoderma. When mature, the ganoderma spores are ejected from the pileus. Such ejected ganoderma spores are collectively called "spore powders". In the wild, the "spore powders" are difficult to collect because of the following reasons: (1) the germination rate (i e., about 3–15%) of the spores is extremely low; (2) the ejection period is relatively short (i.e., approximately 10 days per lifecycle); and (3) some environmental factors, such as wind and rain, may also hinder the collection of the spores. In addition, the substances of the collected spores are difficult to extract due to the resiliency of the epispores.

In recent years, with the improvement of the spore breaking techniques, more research which directed to the studies of the ganoderma spores has been undertaken. However, the improvement of the spore breaking techniques does not overcome the shortcoming of the low germination rate of the spores. In fact, due to the low germination rate, most of the studies on ganoderma spores are conducted using the extraction of bioactive substances from spores representing an array of dormant to various germination stages. Because the spores at different stages of the lifecycle produce different kinds and/or proportions of bioactive substances, each batch of the mixture of the spores thus contains different active ingredients. The results from such studies are apparently meaningless since no proper controls can be provided.

A germination activation method is disclosed in the parent application of the present application, which was issued as U.S. Pat. No. 6,316,002 B1, which is herein incorporated by reference. The method provides successfully activation of the dormant ganoderma spores and increase the germination rate of the ganoderma spores to more than 95%.

Although in the parent applications, GLSs demonstrated therapeutically activities in patients with immunological disorders, which suggested that GLSs may have effect on SLE, which is essentially an immunological disorder, no experimental data were presented in support of that possibility. In the present invention, the therapeutic effects of GLSs to treat SLE are introduced, using allogenic lymphocyte-induced SLE mice (DBA/2 and BALB/C F1 mice) as a model. The results demonstrate that GLSs are capable of relieving the symptoms associated with SLE. The therapeutic effects of GLSs on SLE are similar to, but without the toxic side effects of, corticosteroid such as prednisolone. A combined treatment of GLSs and cortisosteroid is also investigated. The results indicate that the combined treatment of GLSs and corticosteroid restores the T cell counts in the lupus mice to a level comparable to those in the normal mice.

SUMMARY OF THE INVENTION

The present invention provides a method for treating a mammal with immunological disorder by orally administering to the mammal an effective amount of a germination activated Ganoderma Lucidum spores (GLSs). The preferred mammal is human.

The immunological disorder is a disease which includes, without limitation, dysfunction of the nervous system, neuromusculature including multiple sclerosis, myotonias and muscular dystrophy, and autoimmune diseases. The preferred embodiment of this invention involves the treatment of autoimmune diseases. Examples of the autoimmune diseases include, without limitation, rheumatoid arthritis, insulin-dependent diabetes mellitus, acquired immunodeficiency syndrome ("AIDS"), hemolytic anemias, rheumatic fever, Crohn's disease, Guillain-Barre syndrome, psoriasis, thyroiditis, Graves' disease, myasthenia gravis, glomerulonephritis, autoimmune hepatitis, multiple sclerosis, and systemic lupus erythematosus (SLE). The method of the present invention is preferably for treating patients with (SLE).

The preferred dosage of GLSs for treating patients with SLE is in the amount of about 1–20 g of GLSs per person per day, and most favorably 3–12 g per person per day.

The GLSs can be co-administered with a corticosteroid hormone to achieve a better therapeutical activity on relieving/reducing the symptoms associated with SLE.

Examples of corticosteroid hormone include, but are not limited to, prednisolone, prednisone, hydrocortisone, methylprednisolone, and dexamethasone, cortisol, cortisone, triamcinolone, betamethasone, etc. These corticosteroid hormones can be administered by mouth, by topical treatment (such as in solution, cream, lotion or ointment), or by parenteral injection. The preferred corticosteroid is prednisolone, which is preferably administered to patient by mouth.

The GLSs can be used as an agent for treatment of SLE. Alternatively, a combination of GLSs and a corticosteroid hormone can also be used as a treatment regimen to treat SLE.

DETAILED DESCRIPTION OF THE INVENTION

The tiny spore of *Ganoderma lucidum* has an extremely hard and resilient, double-layered epispore. In the wild, the germination of the spores of *Ganoderma lucidum* is relatively slow and their germination rate is extremely low. In fact, it takes about 24 to 48 hours for the germ tubes of the spores start to sprout under proper conditions, and the capillitia start to form branches after 72 hours, with a germination rate of only 3–15%.

Mature spores of *Ganoderma lucidum* were selected to undergo processing treatment. There are three distinctive stages for the spores processing treatment so as to effectively preserve the large amount of bioactive substances produced by the germination activated spores. The first stage involves the induction of germination, which is achieved by soaking the spores in a solution for a period of time, followed by cultivating the germination induced spores in a well-ventillated culture box. The second stage involves the production of sporoderm-broken (i.e., by breaking up the cell walls of epispores) spores, which is achieved by enzyme treatment and/or mechanical force. The final stage involves the extraction of bioactive substances from the sporoderm-broken spores, which is achieved by freeze-drying or vacuum drying followed by extraction with solvent or by thin film condensation.

Below are general descriptions of the steps which lead to the production of bioactive substances:

I. Soaking to induce germination: Mature and perfect spores of *Ganoderma lucidum* were carefully selected to undergo a soaking process to induce germination. Spores were kept in clear or distilled water, biological saline solution, or other nutritional solutions that could enable the spores of red *Ganoderma lucidum* to germinate rapidly. Examples of nutritional solutions include coconut juice or a 1–5% malt extract solution, 0.5–25% extracts of *Ganoderma lucidum* sporocarps or *Ganoderma lucidum* capillitia, 0.1–5% of culture solution containing biotin, 0.1–3% of culture solution containing potassium phosphate (monobasic) and magnesium sulfate. The choice of solution would depend on the soaking time required, the amount of spores to be processed and other such factors as availability of materials. One or more of the above germination solutions could be used, with the amount added being 0.1–5 times the weight of the spores of red *Ganoderma lucidum*. The soaking time was determined according to the temperature of the water, and usually the soaking was carried out for 30 min to 8 hours with the temperature of the water at 20–43° C. Preferably soaking times were 2–4 hours, and temperature of the water was 25–35° C.

II. Activation culture: The spores of *Ganoderma lucidum* were removed from the soaking solution and excess solution was eliminated by allowing it to drip. The spores were then placed in a well-ventilated culturing box at a constant temperature and humidity so that spore activation culture could be carried out. The relative humidity of the culture was generally set at 65–98%, the culture temperature at 18–48° C. and the activation time lasted from 30 min to 24 hours. Preferably humidity is 85–97% and temperature is 25–35° C. Using this method, the activation of spores of red *Ganoderma lucidum* reached a rate of more than 95%. During activation, the cell walls of the spores of red *Ganoderma lucidum* were clearly softened such that it was easier to penetrate the cell walls of the spores.

III. Treatment of the epispores: After the germination activation process, the spores were treated by enzymolysis. This process was carried out at a low temperature and under conditions such that enzyme activity was maintained, using chitinase, cellulase, or other enzymes, which are commonly used in the industry. The process was complete when the epispores lost their resilience and became brittle. Alternatively, physical treatments were carried out to penetrate the cell walls, for example, micronization, roll pressing, grinding, super high pressure microstream treatment, and other mechanical methods commonly used in the industry could be carried out, with a penetration rate of over 99%.

IV. Drying/Encapsulation: Drying was carried out at low temperature using standard methods including freeze-drying or vacuum-drying etc., which are commonly used in the industry. The obtained product had a moisture content less than 4%. The dried GLSs are in powder form and encapsulated. Each capsule contains 300 mg of dried GLSs.

The recommended clinical dosage of GLSs to treat patients with immunological disorders was about 6.3 g/day/person, which was converted according to the respective body mass of humans and mice. This was equivalent to a dosage in mice of 0.8 g/kg, (6.3 g÷7.9=0.8 g/kg). About 10 times the recommended clinical dosage of GLSs did not appear to cause adverse effects in humans and mice.

The present invention uses GLSs to treat immunological disorder, particularly autoimmune disease, and most favorably SLE. SLE is an autoimmune disease also known as Lupus. In patients with SLE, multiple vital organs may be attacked by autoantibodies (also known as "self-reactive antibody") such as anti-dsDNA, SSA/SSB, and Sm/RNP antibodies. Kidneys are eventually involved in about 80% of lupus patient. In lupus nephritis, severe proteinuria, high titers of anti-dsDNA and heavy mono-nuclear infiltration in kidney parenchyma are found in patients.

At present, there is no cure for SLE. The mainstay of lupus treatment involves the use of corticosteroid hormones, such as prednisone, hydrocortisone, methylprednisolone, and dexamethasone. Corticosteroids are related to cortisol, which is a natural anti-inflammatory hormone. They work by rapidly suppressing inflammation. However, cortocosteroids are known for its side effects. Short-term side effects of corticosteroids include swelling, increased appetite, weight gain, and emotional ups and downs; and long-term side effects of corticosteroids can include stretch marks on the skin, excessive hair growth, weakened or damaged bones, high blood pressure, damage to the arteries, high blood sugar, infections, and cataracts.

Other than corticosteroids, several other types of drugs such as non-steroidal anti-inflammatory drugs, COX-2 inhibitors, antimalarials, methotrexate, Gamma globulin, and immunosuppressives, are also commonly used to treat lupus. However, similar to corticosteroid treatment, these other treatment options for lupus also lead to unwanted adverse effects.

The following examples are illustrative, but not limiting the scope of the present invention. Reasonable variations, such as those occur to reasonable artisan, can be made herein without departing from the scope of the present invention. Also, in describing the invention, specific terminology is employed for the sake of clarity. However, the invention is not intended to be limited to the specific terminology so selected. It is to be understood that each specific element includes all technical equivalents which operate in a similar manner to accomplish a similar purpose.

EXAMPLE 1

Immunoregulatory Effect of GLSs

I. Test Conditions:

1. Samples: The dosage for testing the immunoregulatory effect of GLSs was at 0.06 g/kg bodyweight (BW) per day, and the concentrations needed for the various tests were all prepared by diluting GLSs in with distilled water.

2. Dosage Groups: The animals were divided into the cold distilled water control group, and high, medium and low doses groups. The dosage of each group was described as follows:

Low dose group: 0.06 g/kg BW per day.

Medium dose group: 0.60 g/kg BW at approximately 10 times of that in the low dose group.

High dose group: 1.80 g/kg BW at approximately 30 times of that in the low dose group.

3. Animals: NIH small white mice, 6–8 weeks old, weight 20–22 g, supplied by the Guangdong Medical Animal Farm, qualification inspection approval No. 97A022. The pellets were supplied by the Guangdong Medical Animal Farm.

4. Laboratory for animal testing: Clean grade, Guangdong qualification inspection approval no. 96C10, medical animal use no. 26-040. Room temperature 25±2° C., humidity 70–75%.

5. Route of administering the test substances: The test substances were gavaged to each animal at a dose of 0.2 mL/10 g daily.

II. Test Methods:

1. Test of the Delayed Allergic Reaction of the Mouse (by Measuring the Increase of the Thickness of the Footpad)

A week after being examined under laboratory conditions, 40 mice were randomly divided into 4 groups, with 10 for each group. The test substances were administered to the mice every day, with the duration of the test lasting for 4 weeks. Four (4) days before the end of the test, the immune animals were given injections of 0.2 mL 2% (v/v) sheep erythrocytes in the abdomen to sensitize the animals. Four (4) days later the thickness of the left rear footpad was measured, then 20% (v/v) sheep erythrocytes (20 $\mu$L per mouse) were injected subcutaneously at the same location. Twenty four (24) hrs after the injection, the thickness of the left rear footpad was measured three times and a mean value was obtained.

2. Measurement of the Mouse Serum Hemolysin Titer (by Measuring the Blood Coagulation)

Forty (40) mice were randomly divided into 4 groups, with 10 for each group. The test substances were administered every day, with the duration of the test lasting for 4 weeks. The amount of the samples given was adjusted every week according to the increase or decrease of the body weight. Four (4) days before the end of the test, the immune animals were each given injections of 0.2 mL 2% (v/v) sheep erythrocytes in the abdomen, and 5 days later the eyeballs were extracted to obtain blood samples, with the blood serum separated to be used later. The thymus and the spleen were weighed and their ratios to the body weight were calculated.

Coagulation reaction: the blood serum was diluted with biological saline solution at an appropriate ratio in a trace element reaction plate, each 50 $\mu$L, then 50 $\mu$L of 0.5% sheep erythrocytes were added, placed inside a moist container, covered with a lid and placed in an incubator at 37° C. for 3 hrs. The degree of coagulation was observed.

3. Mouse Carbon Clearance Test

Forty (40) mice were randomly divided into 4 groups, with 10 for each group. The test substances were administered every day, with the duration of the test lasting for 4 weeks. The amount of the samples given was adjusted every week according to the increase or decrease of the body weight. On day 28 when the drug was administered for the last time, India ink diluted at 1:4 was intravenously injected into the tail of the mouse at 0.1 mL per 10 g body weight per mouse. Using a timer, 20 $\mu$L blood were drawn at once, at intervals of 2 min and 10 min, from the veins inside the canthus, added to 2 mL $Na_2CO_3$ solution, then the OD value was measured at the 600 nm wavelength using a 721 spectrometer with the $Na_2CO_3$ solution serving as a blank control. The mice were then sacrificed, the liver and the spleen weighed to calculate the phagocytic index.

4. Data Processing: Variance Analysis was Carried out Using the SAS Software Package.

III. Test Results

1. The effect of the GLSs on the body weight of the mice was shown in Table 1. The original, intermediate and the final body weights of the mice of each of the test groups were compared to the control groups for the same periods and statistically processed. The results were insignificant, indicating that the GLSs did not have significant effect on the body weight of the mice.

TABLE 1

Effects of GLSs on the Body Weight of the Mice

| Group | No. of animals (mouse) | Body weight | Thymus/body weight | Spleen/body weight | Control group |
|---|---|---|---|---|---|
| Control group | 10 | 23.0 ± 1.15 | 24.9 ± 0.75 | 27.7 ± 0.95 | 4.8 ± 1.24 |
| Low dose | 10 | 22.9 ± 1.23 | 25.2 ± 0.76 | 28.0 ± 1.34 | 5.1 ± 0.82 |
| Medium dose | 10 | 22.9 ± 1.16 | 25.3 ± 0.65 | 28.5 ± 1.42 | 5.3 ± 0.97 |
| High dose | 10 | 23.2 ± 0.96 | 25.3 ± 0.55 | 27.6 ± 1.46 | 4.6 ± 0.71 |
| F value | | 0.18 | 0.76 | 0.89 | 1.15 |
| p value | | >0.05 | >0.05 | >0.05 | >0.05 |

2. The effect of the GLSs on the spleen and thymus weights of the mice is shown in Table 2. The values of the spleen and the thymus weights of the mice of each of the test groups were compared to the control groups and statistically processed. The results were not significant, indicating that there is no effect of the GLSs on the spleen and thymus weights of the mice.

TABLE 2

The effect of the pure GLSs on the Spleen and Thymus Weights of the Mice

| Group | No. of animals (mouse) | Body weight | Thymus/body weight | Spleen/body weight |
|---|---|---|---|---|
| Control group | 10 | 28.7 | 3.52 ± 0.46 | 4.08 ± 0.82 |
| Low dose | 10 | 27.6 | 3.44 ± 0.37 | 3.85 ± 0.38 |
| Medium dose | 10 | 29.3 | 3.18 ± 0.26 | 4.63 ± 0.75 |
| High dose | 10 | 28.9 | 3.21 ± 0.45 | 4.20 ± 0.88 |
| F value | | | 2.02 | 0.43 |
| p value | | | >0.05 | >0.05 |

3. The effect of the GLSs on the delayed allergic reaction of the mice is shown in Table 3. The thickness of the tested parts of the mice of the low, medium and high dose groups were compared to those of the control group and statistically processed. The differences are highly significant, indicating that the test results were positive.

TABLE 3

The Effect of the GLSs on the Delayed Allergic Reaction of the Mice

| Group | No. of animals (mouse) | Thickness of the left rear footpad Mean ± standard deviation | p value (compared to the control group) |
|---|---|---|---|
| Control group | 10 | 0.43 ± 0.16 | |
| Low dose | 10 | 0.71 ± 0.22 | <0.01 |
| Medium dose | 10 | 0.68 ± 0.10 | <0.01 |

TABLE 3-continued

The Effect of the GLSs on the Delayed Allergic Reaction of the Mice

| Group | No. of animals (mouse) | Thickness of the left rear footpad Mean ± standard deviation | p value (compared to the control group) |
|---|---|---|---|
| High dose | 10 | 0.77 ± 0.19 | <0.01 |
| F value | | 7.70 (P < 0.01) | |

Note: p value is the result of q test, and the comparison of each test group with the control groups 4. The effect of the GLSs on the antibody titer of the blood serum hemolysin of the test animals is shown in Table 4. The high dose group of the test was compared to the control group and the differences were highly significant, indicating that the effect of the GLSs on the antibody titer of the blood serum hemolysin of the test animals was positive.

TABLE 4

The effect of the GLSs on the Antibody Titer of the Blood Serum Hemolysin

| Group | No. of Animals (mouse) | Antibody product Mean | ± | Standard Deviation | p value (compared to the control group) |
|---|---|---|---|---|---|
| | | | ± | | |
| Control Group | 10 | 72.6 | ± | 17.59 | |
| Low dose | 10 | 87 | ± | 13.7 | >0.05 |
| Medium dose | 10 | 89.6 | ± | 13.43 | >0.05 |
| High dose | 10 | 103.4 | | 16.19 | <0.01 |
| F value | | | | | |

Note: p value is the result of q test, and the comparison of each test group with the control groups.

5. The effect of the GLSs on the carbon clearance phagocytic index of the mice is shown in Table 5. The high dose group of the test was compared to the control group. The differences were highly significant, indicating that the GLSs could significantly increase the carbon clearance phagocytic index of the test animals.

TABLE 5

The effect of the GLSs on the Carbon Clearance Phagocytic Index of Mice

| Group | No. of Animals (mouse) | Carbon clearance phagocytic index Mean | ± | Standard Deviation | p value (compared to the control group) |
|---|---|---|---|---|---|
| Control Group | 10 | 4.59 | ± | 0.34 | |
| Low dose | 10 | 4.7 | ± | 0.59 | >0.05 |

TABLE 5-continued

The effect of the GLSs on the Carbon Clearance Phagocytic Index of Mice

| Group | No. of Animals (mouse) | Carbon clearance phagocytic index Mean | ± | Standard Deviation | p value (compared to the control group) |
|---|---|---|---|---|---|
| Medium dose | 10 | 5.01 | ± | 0.21 | >0.05 |
| High dose | 10 | 5.2 | ± | 0.39 | >0.05 |
| F value | | | | | |

Note: p value is the result of q test, and the comparison of each test group with the control groups.

IV. Conclusion:

By using the GLSs, the delayed allergic reaction of the mice (Table 3) induced by the sheep erythrocytes, was significantly increased (as measured by the increase in the thickness of the footpad), indicating an effect on increasing the immune function in the mice. Also, the antibody titer of the blood serum hemolysin of the mice (Table 4) was significantly elevated, indicating an effect on increasing the humoral immune function. Finally, the carbon clearance phagocytic index of the mice (Table 5) was significantly increased, indicating an effect on increasing the phagocytosis by the phagocytes.

The results show that the GLSs exhibit an immunoregulatory effect.

EXAMPLE 2

Test of GLSs Toxicity and Mutagenicity in Mice

I. Material:

1. Test material: The GLSs were brown powders. After going through a 100 mesh sieve, 120 g of the samples were mixed with 300 mL distilled water (to give a concentration of 40 g/dL) and stirred for 15 min in a stirrer at 7000 rpm. They were then bottled, underwent disinfection and antiseptic treatments, and 1 mL of a pasty liquid was obtained, which was about 0.4 g of the samples. Direct gavage was carried out two times per day.

2. Animals: Healthy NIH small white mice supplied by the Guangdong Medical Animals Farm, with body weights of 18–22 g.

II. Methods and Results:

1. Mouse Acute Toxicity $LD_{50}$ Test:

Forty (40) NIH small white mice with body weights of 18–22 g, half male and half female, were used in this test. Using Horn's method, the mice were randomly divided into 4 dose groups and were force fed once on empty stomachs. Observation was carried out for a week and the results are shown in Table 6.

TABLE 6

Acute Toxicity Test Results

| Dose (g/kg) | No. of animals (mouse) Female | Male | No. of deal animals (mouse) Female | Male |
|---|---|---|---|---|
| 21.50 | 5 | 5 | 0 | 0 |
| 10.00 | 5 | 5 | 0 | 0 |
| 4.64 | 5 | 5 | 0 | 0 |
| 2.15 | 5 | 5 | 0 | 0 |

Result: The activity and feeding of the test mice appeared normal. There was no deaths. $LD_{50}>21.5$ g/kg BW was obtained by administration to both male and female mice via the oral route.

The results demonstrate that the sampled GLSs contained nontoxic substances. The amount was 268.75 times the recommended treatment amount (0.08 g/kg BW).

2. Mouse Bone Marrow Micronucleus Test:

Seventy (70) NIH mice with body weights of 20–23 g were used in this test. The mice were divided into 7 groups and testing was carried out according to the methods of the Toxicological Evaluation Procedures for Food Safety. Gavage was carried out twice, and 6 hrs after the second force feeding, the mice were sacrificed, and both of the femurs were taken out for the preparation of a biopsy, staining and examination under a microscope. The micronucleus rate of each of the groups was calculated and the results were shown in Table 7.

Result: The micronucleus rate of the various dose groups of the GLSs was similar to that of the blank control group and none of them showed a significant difference. The test showed a negative result.

TABLE 7

Mouse Bone Marrow Micronucleus Test Results

| Dose (g/kg) | No. of animals | No. of test cells stained red | No. of micronuclei | Percentage of micronuclei |
|---|---|---|---|---|
| | | | | (0/00) |
| 0 | | | | |
| 10.00 | 5 | 5 | 10000 | 14 | 1.4 |
| 5.00 | 5 | 5 | 10000 | 15 | 1.5 |
| 2.50 | 5 | 5 | 10000 | 14 | 1.4 |
| 1.25 | 5 | 5 | 10000 | 13 | 1.3 |
| 0.62 | 5 | 5 | 10000 | 14 | 1.4 |
| Endoxan (0.06) | 5 | 5 | 10000 | 12 | 1.2 |
| | 5 | 5 | 10000 | 249 | 24.9** |

**The blank control group and the various dose groups compared to the positive Enoxan group p < 0.001. Bilateral T-test statistical processing was used.

3. Sperm Deformation Test

Twenty five (25) NIH mice with body weights of 18–22 g, randomly divided into 5 groups and continuously force fed for 5 days (the Endoxan positive group received abdominal injections), were used in this test. Thirty five (35) days later, the animals were sacrificed and both testicles were taken out for the standard biopsy preparation and staining. Five thousand (5000) whole sperm from each group were examined under an oil immersion lens and the sperm deformation percentage was calculated. The results are shown in Table 8.

TABLE 8

Analysis of the Effect of the GLSs on the Mouse Sperm Deformation Test

| Dose (g/kg) | No. of animals (mouse) | No. of test sperm (count) | No of deformed sperm (count) | Percentage deformation |
|---|---|---|---|---|
| 0 | 5 | 5000 | 98 | 19.60 |
| 10.00 | 5 | 5000 | 98 | 19.60 |
| 5.00 | 5 | 5000 | 98 | 18.80 |
| 2.50 | 5 | 5000 | 98 | 18.40 |
| Endoxan (0.04) | 5 | 5000 | 98 | 72.80** |

**According to the Wilcoxon sequence test result, the blank control group and the various dose groups compared to the Endoxan group $p < 0.01$.

Result: The sperm deformation percentage of the various dose groups of the GLSs was similar to that of the blank control group. Even when a dose as high as 50.00 g/kg BW of GLSs was used, no induced deformation of the reproductive cells was found.

4. Ames Test

Test bacteria (TA97, TA98, TA100, TA102) were supplied by the Bureau of Food Inspection, Department of Health in Beijing. Some of the properties and the S9 activity of the bacteria were evaluated and they met the requirement. Using the Petri dish mixing method, two independent tests were carried out. Three dishes were prepared for each group and the results are shown in Table 9.

Result: Whether or not S9 mixtures were added to each of the dose groups of the pure *Ganoderma lucidum* spore capsules (cell wall completely penetrated), the test results showed that the number of colonies due to reverse mutation was never more than 2 times the number of colonies due to natural mutation. There was no indication that the GLSs could cause mutations directly or indirectly.

TABLE 9

Test Result of the GLSs Using the Petri Dish Mixing Method

| Dosage Mg/dish | TA97 +S9 | TA97 −S9 | TA98 +S9 | TA98 −S9 | TA100 +S9 | TA100 −S9 | TA102 +S9 | TA102 −S9 |
|---|---|---|---|---|---|---|---|---|
| 5000 | 149 | 135 | 33 | 32 | 180 | 167 | 311 | 296 |
| 500 | 154 | 141 | 37 | 34 | 148 | 152 | 311 | 195 |
| 50 | 161 | 152 | 47 | 36 | 175 | 164 | 305 | 288 |
| 5 | 149 | 153 | 35 | 30 | 167 | 159 | 299 | 267 |
| 0.5 | 164 | 159 | 38 | 35 | 153 | 146 | 305 | 288 |
| Natural reverse mutation | | 142 | | 39 | | 154 | | 297 |
| Positive control Atabrine | | >1500 | | >1433 | | | | |
| Sodium azide | | | | | | >1500 | | |
| Mitomycin | | | | | | | | >1500 |
| 2-Amino-fluorine | >1500 | | >1600 | | >1500 | | >855 | |

IV. Summary of Test Results:

1. $LD_{50}$:

No adverse effects were observed for the animals and $LD_{50} > 21.5$ g/kg BW was obtained when the samples were given to male and female mice via the oral route. This is roughly equal to a $LD_{50}$ of 170 g in human. These results demonstrate that the sampled GLSs are nontoxic.

2. Micronucleus Test

The micronucleus rate of 0.62–10 g/kg BW GLSs was compared to that of the blank control group, and no significant differences were found. The test showed a negative result. There was no mutation of the cells of the body induced by GLSs.

3. Sperm Deformation Test

The sperm deformation rate of 2.5–10 g/kg BW GLSs was compared to that of the blank control, and no significant differences were found. The test showed a negative result; there was no induced deformation of the reproductive cells of the body by GLSs.

4. Ames Test

Whether or not S9 mixtures were added to 0.5–5000 μg/dish GLSs, the test results showed that the number of colonies due to reverse mutation was never more than 2 times the number of colonies due to natural mutation. The results also show that GLSs did not cause mutations directly or indirectly.

EXAMPLE 3

Toxicology Tests of *Ganoderma* in Rats

I. Material:

1. Test material: The GLSs samples were as brown powders. After going through a 100 mesh sieve, 120 g of the samples were mixed with 300 mL distilled water and stirred at high speed for 15 min at 7000 rpm. They were then subjected to disinfecting and antiseptic treatments for 20 min, and made into pastes. One (1) mL of the paste was about 0.4 g of the samples.

2. Animals: Healthy SD rats supplied by the Guangdong Medical Animals Farm.

II. Methods:

Ninety six (96) healthy SD rats with body weights of 80–88 g were selected, which were supplied by the Guangdong Medical Animal Farm. They were randomly divided into 4 groups with 24 rats in each group, half male and half female. The average difference in body weight in each of the group was less than ±5 g. Observation was carried out for 1 week before the administration of the drug to see if there were any abnormal activities, feeding or characteristic appearances among the animals of the different dose groups.

1. Dosage: The recommended treatment amount was 4 times every day, 4 capsules each time and 0.3 g per capsule, based on an adult of 60 kg, at about 0.08 g/kg BW. Three test groups and a control group were set up respectively for the male and the female rats with 12 rats for each group.

Blank control group: Distilled water
25× group: 2.0 g/kg/day
50× group: 4.0 g/kg/day
100× group: 8.0 g/kg/day 2. Test Methods:

(1) Gavage of the samples was administered every day according to the body weight. The high dose group was gavaged twice every day and the control group was gavaged the same amount of distilled water. The samples were administered continuously for 30 days. The body weights were taken every week and the amount of the feed consumed was calculated while tracking the physiological indexes of the animals.

(2) Standard blood tests were carried out at the end of the test, the test items included the erythrocyte counts, hemochrome, white cell counts, the kind, and number of platelets, measured by the R-1000SYSME blood cell counter made in Japan. For the blood biochemical indexes, blood sugar, albumin, triglycerides, total cholesterol, dehydrated creatine, glutamate-pyruvate transaminase and urea nitrogen were tested. Measurements were carried out using the ALIZE automatic biochemical analyzer made in France.

(3) The liver, kidney, spleen, heart and testicles were extracted and weighed, preserved in formaldehyde, and the standard biopsies were taken, stained so that pathological changes could be observed.

III. Result and Analysis:

1. The rats from the different dose groups grew well and there were no significant differences when compared to the control group ($p>0.05$) (See Tables 10 and 11). The consumption of the feed by the rats of each of the dose groups and the utilization rate of the food also showed no significant differences when compared to the control group (See Table 12).

2. In the final hemogram test, none of the specific indexes showed any significant differences when compared to the control group (See Table 13).

3. In the items of the blood biochemical indexes, the blood sugar levels of the male rats were decreased in the low and medium dose groups and there were significant differences when compared to the control group ($p<0.01$). The blood sugar level of the male rats was decreased in the high dose group and there was a significant difference when compared to the control group ($p<0.05$). The blood sugar level of the female rats was decreased in the low dose group and there was a significant difference when compared to the control group ($p<0.01$). The blood sugar levels of the female rats were decreased in the medium and high dose groups and there were significant differences when compared to the control group ($p<0.05$). However, these biochemical changes basically varied within the normal range. There were significant differences in the urea nitrogen content of the male rats in the low and medium dose groups when compared to the control group ($p<0.05$). There were significant differences in the triglyceride content of the female rats in the low and high dose groups when compared to the control group ($p<0.05$). There were no significant differences in the other indexes of any of the test groups when compared to the control group (See Table 14).

4. There were no significant differences in the organ indexes of each of the test groups when compared to the control group (See Table 16). Pathological observation showed that there were no pathological abnormalities of the organs in any of the test groups.

TABLE 10

Change in Body Weight of the Rats After GLSs Administration (Each Group n = 12, X ± SD

| Sex | Group | Original body weight | First week | Second week | Third week | Forth week |
| --- | --- | --- | --- | --- | --- | --- |
| Male rats | Control | 87 ± 9.4 | 120.2 ± 11.0 | 152.1 ± 12.9 | 192.0 ± 13.4 | 242.3 ± 17.6 |
| | 10 Times | 88.0 ± 6.7 | 125.1 ± 9.3 | 145.0 ± 9.9 | 190.6 ± 11.5 | 242.0 ± 18.2 |
| | 50 Times | 85.7 ± 8.6 | 125.8 ± 15.2 | 148.4 ± 12.1 | 192.9 ± 12.2 | 235.5 ± 24.0 |
| | 100 Times | 86.6 ± 8.9 | 123.0 ± 13.7 | 154.7 ± 17.0 | 202.2 ± 18.3 | 251.6 ± 25.8 |
| Female rats | Control | 82.4 ± 7.5 | 109.2 ± 8.0 | 148.8 ± 8.2 | 165.1 ± 18.3 | 202.6 ± 16.1 |
| | 10 Times | 80.5 ± 7.3 | 117.7 ± 9.2 | 144.3 ± 9.9 | 174.2 ± 12.0 | 206.2 ± 11.5 |
| | 50 Times | 80.5 ± 5.9 | 112.4 ± 15.2 | 141.2 ± 9.9 | 171.5 ± 13.1 | 199.6 ± 17.2 |
| | 100 Times | 81.7 ± 6.6 | 115.3 ± 13.0 | 144.1 ± 14.7 | 171.5 ± 16.2 | 206.8 ± 24.9 |
| F Value | Male | 0.15 | 0.48 | 0.75 | 1.33 | 1.27 |
| | Female | 0.21 | 2.73 | 1.01 | 0.94 | 0.45 |

TABLE 11

Change in Body Weight, Feed Consumption and Utilization in Rats
After GLSs Administration, each group n = 12, X ± SD

| Sex | Group | Original body weight | Final body weight (g) | Increase in the body weight (g) | Amount of feed consumed (g/mouse) | Utilization of the food |
|---|---|---|---|---|---|---|
| Male rats | Control | 87 ± 9.4 | 242.3 ± 17.6 | 155.2 ± 20.1 | 596.4 | 26.02 |
| | 25 Times | 88.0 ± 6.7 | 242.0 ± 18.2 | 154.0 ± 15.5 | 656.7 | 23.45 |
| | 50 Times | 85.7 ± 8.6 | 235.5 ± 24.0 | 149.8 ± 24.3 | 625.6 | 23.95 |
| | 100 Times | 86.6 ± 8.9 | 251.6 ± 25.8 | 165.1 ± 19.5 | 640.9 | 25.76 |
| Female rats | Control | 82.4 ± 7.5 | 201.6 ± 16.1 | 119.2 ± 16.1 | 552.8 | 21.56 |
| | 25 Times | 80.5 ± 7.3 | 206.2 ± 11.5 | 125.7 ± 11.8 | 574.8 | 21.87 |
| | 50 Times | 80.5 ± 5.9 | 199.6 ± 17.2 | 119.1 ± 14.7 | 569.2 | 20.92 |
| | 100 Times | 81.7 ± 6.6 | 206.8 ± 24.9 | 125.1 ± 25.5 | 565.7 | 22.11 |

Net increase in body weight of the male rats  F = 1.27  $P > 0.05$   Net increase in body weight of the male rats  F = 1.12  $P > 0.05$

TABLE 12

Standard blood indexes, each group n = 12, X ± SD

| | Group | Red Blood Cells | Hemoglobin | Blood platelets | White blood cells | Lymphocytes | Mid-illegible cells | Neutrophilis |
|---|---|---|---|---|---|---|---|---|
| Male rats | Control | 6.84 ± 0.36 | 124.2 ± 10.1 | 106.2 ± 167.4 | 7.17 ± 1.23 | 90.4 ± 5.4 | 5.5 ± 3.2 | 4.1 ± 2.4 |
| | 25 Times | 6.57 ± 0.51 | 122.2 ± 13.8 | 931.8 ± 90.9 | 10.85 ± 3.53 | 90.9 ± 3.8 | 4.3 ± 1.7 | 4.8 ± 2.5 |
| | 50 Times | 6.51 ± 0.41 | 122.5 ± 14.1 | 981.7 ± 190.3 | 9.40 ± 1.86 | 90.6 ± 3.9 | 4.8 ± 1.7 | 4.6 ± 2.7 |
| | 100 Times | 6.71 ± 0.38 | 123.2 ± 10.6 | 1169.8 ± 254.2 | 8.12 ± 2.00 | 91.8 ± 2.5 | 4.8 ± 1.4 | 3.9 ± 1.6 |
| Fem. Rats | Control | 6.74 ± 0.66 | 132.0 ± 10.1 | 1155.7 ± 196.3 | 9.63 ± 3.39 | 91.3 ± 4.7 | 4.3 ± 2.0 | 4.4 ± 2.8 |
| | 25 Times | 6.32 ± 0.62 | 126.1 ± 2.9 | 1202.5 ± 256.6 | 10.68 ± 2.89 | 83.6 ± 2.8 | 3.9 ± 1.6 | 3.7 ± 1.2 |
| | 50 Times | 6.43 ± 0.91 | 133.2 ± 9.2 | 1241.8 ± 199.6 | 8.73 ± 1.79 | 90.3 ± 4.4 | 4.8 ± 1.8 | 4.8 ± 3.2 |
| | 100 Times | 6.33 ± 0.50 | 127.8 ± 7.7 | 1440.2 ± 377.5 | 10.42 ± 1.19 | 92.2 ± 4.2 | 4.1 ± 1.9 | 3.8 ± 2.4 |

White blood cells  F = 5.14  $P < 0.01$  Compared to the control group  $P < 0.05$

TABLE 13

Biochemical indexes, each group n = 12, X ± SD

| | Group | Blood sugar | Triglycerides | Total cholesterol | Urea Nitrogen | Glutamate pyruvate transaminase | Blood serum albumin | Muscle anhydride |
|---|---|---|---|---|---|---|---|---|
| Male rats | Control | 3.71 ± 0.59 | 1.41 ± 0.37 | 1.78 ± 0.23 | 10.29 ± 1.61 | 51.0 ± 7.6 | 38.09 ± 1.42 | 66.76 ± 4.91 |
| | 25 Times | 2.65 ± 0.67 | 1.67 ± 0.44 | 1.98 ± 0.30 | 8.64 ± 1.32 | 55.8 ± 10.5 | 40.73 ± 1.72 | 65.57 ± 6.52 |
| | 50 Times | 2.75 ± 0.41 | 1.63 ± 0.42 | 1.90 ± 0.41 | 8.40 ± 1.58 | 55.8 ± 11.7 | 41.42 ± 1.39 | 66.57 ± 5.52 |
| | 100 Times | 3.08 ± 0.48 | 1.36 ± 0.39 | 1.73 ± 0.36 | 9.44 ± 2.07 | 59.1 ± 10.9 | 40.91 ± 0.91 | 67.56 ± 4.91 |
| Fem. rats | Control | 4.92 ± 0.63 | 0.79 ± 0.18 | 1.83 ± 0.29 | 8.88 ± 1.50 | 48.0 ± 8.3 | 40.72 ± 0.96 | 70.60 ± 6.26 |
| | 25 Times | 3.75 ± 0.59 | 1.10 ± 0.25 | 1.94 ± 0.28 | 9.24 ± 0.95 | 53.8 ± 11.9 | 40.28 ± 1.44 | 70.33 ± 4.23 |
| | 50 Times | 4.24 ± 0.37 | 0.92 ± 0.20 | 1.78 ± 0.22 | 9.99 ± 1.42 | 54.1 ± 6.9 | 41.69 ± 1.38 | 73.98 ± 6.14 |
| | 100 Times | 4.27 ± 0.55 | 1.02 ± 0.23 | 1.99 ± 0.39 | 8.95 ± 2.07 | 51.6 ± 13.2 | 41.85 ± 2.56 | 74.84 ± 5.31 |
| | F value  Male 7.08 | 0.05 | 1.32 | 4.49 | 1.26 | 0.78 | 0.28 | |
| | Female 9.60 | 4.59 | 1.19 | 1.3 | 0.03 | 2.42 | 1.64 | |

TABLE 14

Comparison of the organ indexes, each group n = 12, X ± SD

| | Group | Heart | Liver | Spleen | Kidney | Testicles |
|---|---|---|---|---|---|---|
| Male rats | Control | 0.31 ± 0.03 | 2.67 ± 0.18 | 0.24 ± 0.03 | 0.63 ± 0.05 | 0.86 ± 0.09 |
| | 25 Times | 0.31 ± 0.03 | 2.60 ± 0.18 | 0.26 ± 0.05 | 0.64 ± 0.04 | 0.82 ± 0.12 |
| | 50 Times | 0.30 ± 0.03 | 2.60 ± 0.45 | 0.24 ± 0.05 | 0.65 ± 0.07 | 0.87 ± 0.14 |
| | 100 Times | 0.31 ± 0.03 | 2.65 ± 0.17 | 0.21 ± 0.02 | 0.63 ± 0.05 | 0.86 ± 0.08 |
| Female rats | Control | 0.32 ± 0.02 | 2.44 ± 0.23 | 0.26 ± 0.05 | 0.63 ± 0.10 | |
| | 25 Times | 0.31 ± 0.03 | 2.47 ± 0.72 | 0.27 ± 0.03 | 0.64 ± 0.06 | |

TABLE 14-continued

Comparison of the organ indexes, each group n = 12, X ± SD

| Group | Heart | Liver | Spleen | Kidney | Testicles |
|---|---|---|---|---|---|
| 50 Times | 0.33 ± 0.04 | 2.24 ± 0.78 | 0.25 ± 0.78 | 0.67 ± 0.08 | |
| 100 Times | 0.33 ± 0.03 | 2.45 ± 0.34 | 0.25 ± 0.05 | 0.64 ± 0.07 | |

IV. Summary of Test Results

In the present test, 25, 50 and 100 times the recommended amount (0.08 g/kg BW) of the GLSs were administered respectively to growing SD rats of both male and female. The control group was given distilled water. The duration of the test lasted for 30 days and the final results were:

1. Compared to the control group, there was no significant difference in the increase in body weight of the test rats given the pure *Ganoderma lucidum* spores.

2. The standard blood test showed a basically normal result.

3. The biochemical blood serum test: there was a slight decrease in the blood sugar, a slight increase in the triglycerides for the female but these were within the normal range.

4. Examination of the pathological biopsies of the organs of the rats from each of the dose groups showed no abnormalities.

Conclusions: Examination of the 30 days feeding with GLSs showed that all the indexes were normal, and they could be safely used.

EXAMPLE 4

Induction of SLE in Mice

SLE mice was induced by infusing to F1 mice allogenic (different individuals of the same species) T-lymphocytes from DBA/2 and BALB/C mice (parent mice). After a period of time, autoantibodies were found and SLE-like symptoms developed in the F1 mice. SLE-mice demonstrated SLE-like symptoms such as severe proteinuria, high titers of anti-dsDNA autoantibodies, IgG immune complexes precipitated at the base membranes of kidney and skin, and heavy mono-nuclear infiltration in kidney parenchyma, etc., which were essentially the same as those found in lupus patients.

The detailed procedure for inducing the SLE in mice was described as follows:

1. Isolation of Lymphocytes:

Spleens, lymph nodes, and thymus glands were collected under sterile conditions from the DBA/2 or BALB/C mice. Lymphocytes were then isolated and washed with Hanks solution 3 times. Cells were stained with 0.5% trypan blue and examined for viability. The lymphocytes were then adjusted to the desired concentrations.

2. Allogenic Lymphocyte Inoculation:

Mice were randomly separated into 8–10 animals per group. The isolated lymphocytes were infused through vein into unradiated F1 mice which were of the same gender and age. Each animal received two lymphocyte infusions, with 1 week apart. Control group was consisted of unradiated, untreated mice of the same age.

3. Establishment of SLE Mice:

The mice were monitored for the levels of serum autoantibodies and urine proteins. When the symptoms were established (about 2 months), the kidney tissues were collected for pathology and immunology examinations.

EXAMPLE 5

Effects of GLSs and/or Prednisolone on SLE Mice

I. Materials

Fifty (50) female SLE mice, 8 weeks of age and weighing 20–25 g, were obtained from the Experimental Animal Center of the First Military Medical University according to the protocol described in Example 4.

GLSs solution (0.2 g/mL) was obtained from Guangzhou Green Food Project Company of the College of Life Sciences, Zhongshan University and Green Power Health Products International Co. Ltd., Sweden and Hong Kong. Prednisolone (50 mg/100 mL solution) was given to the SLE mice about 50 ml/kg/day.

II. Method

The SLE mice were randomly divided into 4 groups (10 mice per group). Ten normal BALALC mice (the F1 mice without allogenic T-lymphocyte infusion) at the same age and sex of the SLE mice were also used as normal control.

Groups A: normal control;

Group B: SLE control;

Group C: prednisolone alone;

Group D: GLSs alone; and

Group E: prednisolone and GLSs combined treatment.

At about 1.5 hours prior to the experiment, blood samples from each animals in each group were taken, and the symptoms and characteristics of each animals were recorded. The mice in Groups A and B were given saline solution orally; the mice in Group C were given 50 mL/kg/day of prednisolone solution (about 25 mg of prednisolone); the mice in Group D were given 0.8g/kg/day orally; and the mice in Group E were given 50 mL/kg/day of prednisolone and 0.8 g/kg/day of GLSs. The drug was given to the mice daily at 9 am.

At 168 hours after the first dosing, blood samples were collected via tail cutting and T cell counts were performed. Kidney tissues were sampled and undergone morphologic analyses under light scope.

Statistical analyses and t test, were carried out using SPAAS 10.0 computer software.

III. Results

The total T cell (T) (also known as the "T-lymphocyte populations"), T helper cell (Th) and T suppressor (Ts) counts of the blood samples drawn at 168 hours after the first dosing were presented in Table 1.

TABLE 15

Comparison of the T-lymphocyte Populations
in SLE Mice under Different Treatments

| Group | N | T(%) | Th (%) | Ts (%) | Th/Ts |
|---|---|---|---|---|---|
| A (normal control) | 10 | 62.43 ± 3.21 | 38.20 ± 4.91 | 24.20 ± 3.17 | 1.61 ± 0.28 |
| B (SLE control) | 6 | 44.42 ± 2.31 | 25.33 ± 3.38 | 33.23 ± 5.61 | 0.78 ± 0.21 |
| C (prednisolone) | 8 | 51.30 ± 4.23 | 31.44 ± 3.21 | 28.43 ± 3.12 | 1.12 ± 0.31 |
| D (GLSs) | 8 | 53.42 ± 3.32 | 31.32 ± 5.96 | 28.56 ± 6.71 | 1.14 ± 0.25 |
| E (GLSs + prednisolone) | 10 | 60.20 ± 5.43 | 34.53 ± 4.92 | 25.53 ± 4.32 | 1.38 ± 0.17 |

As shown in Table 15, the SLE control group contained the lowest levels of T-lymphocyte populations (T %) and Th %, as well as the lowest Th/Ts ratio. The T %, Th %, Ts % and the Th/Ts ratio in Group C (with GLSs) and Group D (with prednisolone) were similar, which were much better than those in the SLE control group. The most significant improvement came from Group E (with GLSs and prednisolone) where the T %, Th %, Ts %, and Th/Ts ratio were about the same as those in the normal control group (Group A).

IV. Discussion

Ganoderma spores are tiny mist-like spores released by mature Ganoderma. They contain all the bioactive genetic materials of Ganoderma. They can rapidly activate the nerve system, induce feedback regulation, improve endocrine system functions and promote metabolism, thus, increase the immune ability, prevent diseases and delay aging of the body. However, because Ganoderma spores have very strong, tough sporoderms that are resistant to high pressure, acid, and enzymatic digestion. The germination activated Ganoderma lucidum spore powder (GLSs) used in this study had a sporoderm-broken rate higher than 99.8%. The active materials, weighing about 37.5% of the spores, in GLSs maintained their activities after the sporoderms were broken.

The present study results indicated that GLSs treatment could lower the body temperature, stimulate appetite, improve diarrhea, and reduce death rate in SLE mice to certain degrees. Also, no side effect was observed in animals treated with GLSs. Similar to the GLSs treatment, the prednisolone treatment also improved the T cell counts in similar degree as those of GLSs.

However, in SLE mice receiving the combined treatment of GLSs and prednisolone (Group E), the general health and reduction of death (no death in this group) were significantly improved; the T %, Th %, and Th/Ts ratio were increased; and the Ts % was significantly decreased ($p<0.05$), as compared to the SLE control (Group B).

Activation of B cells by T cells has been suggested to the one of the reasons for causing SLE. For this reason, a restoration of the normal homeostasis of T and B cells as well as their cytokines could essentially alleviate the symptoms associated with SLE. Thus, higher number of lymph cells indicate that more numbers of mature T cells and a better immune function are in the body.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A method for treating a mammal with an immunological disorder comprising:

orally administering to said mammal an effective amount of germination-activated, sporoderm-broken *Ganoderma Lucidum* spores (GLSs) to relieve symptoms associated with said immunological disorder;

whereby said germination-activated, sporoderm-broken GLSs are prepared by: soaking *ganoderma* spores in a solution to cause said spores to germinate, cultivating said germinated *ganoderma* spores in a well ventilated culture box to enhance production of bioactive substances in said germinated *ganoderma* spores, and breaking sporoderms of the germination activated *ganoderma* spores to produce said germination-activated, sporoderm-broken GLSs.

2. The method according to claim 1, wherein said immunological disorder is an autoimmune disease.

3. The method according to claim 2, wherein said autoimmune disease is a systemic lupus erythematosus (SLE).

4. The method according to claim 1, wherein said mammal is a mice.

5. The method according to claim 1, wherein said mammal is a human.

6. The method according to claim 5, wherein said germination-activated, sporoderm-broken GLSs are administered in the amount of about 1–20 g per day per person.

7. The method according to claim 6, wherein said germination-activated, sporoderm-broken GLSs are administered in the amount of about 3–12 g per day per person.

8. The method according to claim 3, further comprising administering corticosteroid to said mammal.

9. The method according to claim 8, wherein said corticosteroid is administered to said mammal orally, topically, or by injection.

10. The method according to claim 7, wherein said corticosteroid is prednisolone.

11. The method according to claim 10, wherein said prednisolone is orally administered.

12. The method according to claim 1, wherein said germination-activated, sporoderm-broken GLSs are prepared by treating said germination-activated, sporoderm-broken GLSs with an enzyme with cell wall dissolving property or a mechanical force.

13. The method according to claim 12, wherein said enzyme is chitinase or cellulose.

14. The method according to claim 12, wherein said mechanical force is at least one selected form the group consisting of micronization, roll pressing, ultrasound, and super high pressure microstream treatment.

15. The method according to claim 1, wherein said germination activated, sporoderm-broken GLSs are placed in said culture box at relative humidity of about 65–98% and temperature of 18–45° C.

16. A treatment regimen for treatment of systemic lupus erythematosus (SLE) in a patient comprising:
- co-administering an effective amount of germination-activated, sporoderm-broken *Ganoderma lucidum* spores (GLSs) and a corticosteroid to said patient to relieve symptoms associated with said SLE;
- whereby said germination-activated, sporoderm-broken GLSs are prepared by:
  - soaking *ganoderma* spores in a solution to cause said spores to germinate,
  - cultivating said germinated *ganoderma* spores in a well ventilated culture box to enhance production of bioactive substances in said germinated *ganoderma* spores, and
  - breaking sporoderms of the germination activated *ganoderma* spores to produce said germination-activated, sporoderm-broken GLSs.

17. The treatment regimen according to claim 16, wherein said germination-activated, sporoderm-broken GLSs are administered orally.

18. The treatment regimen according to claim 17, wherein said corticosteroid is administered orally, topically, or by injection.

19. The treatment regimen according to claim 17, wherein said corticosteroid is prednisolone.

20. The treatment regimen according to claim 19, wherein said prednisolone is administered orally.

* * * * *